United States Patent [19]

Suzuki et al.

[11] Patent Number: 5,600,027
[45] Date of Patent: Feb. 4, 1997

[54] PROCESS FOR PRODUCING OPTICALLY ACTIVE ALCOHOL CONTAINING PHENYL GROUP

[75] Inventors: Junko Suzuki, Kanagawa; Satoshi Negishi, Tokyo; Seiichi Shirasawa, Kanagawa; Yukie Masuda, Tokyo, all of Japan

[73] Assignee: The Nisshin Oil Mills, Ltd., Tokyo, Japan

[21] Appl. No.: 529,071

[22] Filed: Sep. 15, 1995

[30] Foreign Application Priority Data

| Nov. 29, 1994 | [JP] | Japan | 6-317695 |
| Nov. 29, 1994 | [JP] | Japan | 6-317696 |
| Nov. 29, 1994 | [JP] | Japan | 6-317697 |
| Nov. 29, 1994 | [JP] | Japan | 6-317698 |

[51] Int. Cl.$^6$ ............................................. C07C 29/74
[52] U.S. Cl. ............................................. 568/810
[58] Field of Search ............................................. 568/810

[56] References Cited

U.S. PATENT DOCUMENTS

| 4,665,029 | 5/1987 | Iwai et al. . |
| 5,032,523 | 7/1991 | Amano et al. . |
| 5,047,346 | 9/1991 | Kitazume et al. . |
| 5,189,204 | 2/1993 | Kitazumo et al. . |
| 5,256,569 | 10/1993 | Yoshida et al. . |

FOREIGN PATENT DOCUMENTS

| 58-36953 | 8/1983 | Japan . |
| 59-156282 | 9/1984 | Japan . |
| 60-15312 | 4/1985 | Japan . |
| 62-166898 | 7/1987 | Japan . |
| 63-173597 | 7/1988 | Japan . |
| 1-137996 | 5/1989 | Japan . |
| 1-257484 | 10/1989 | Japan . |
| 2-86797 | 3/1990 | Japan . |

*Primary Examiner*—Samuel Barts
*Attorney, Agent, or Firm*—Nikaido, Marmelstein, Murray & Oram LLP

[57] ABSTRACT

A process for producing an optically active alcohol having a phenyl group is disclosed, comprising the step of carrying out interesterification between (a) a monoester between a racemic alcohol having a phenyl group and a fatty acid or a diester between a racemic alcohol having a phenyl group and a dibasic acid and (b) an optically inactive non-racemic alcohol having 16 or more carbon atoms in the presence of heat-resistant lipase and in the absence of a solvent under a substantially water-free condition at a temperature of not lower than 81° C. under atmospheric pressure or reduced pressure and the step of separating an optically active alcohol having a phenyl group rich in either one of R- and S-forms from the reaction mixture. Use of heat-resistant lipase makes it possible to use high-melting point materials without using any solvent therefor and to perform interesterification at a high temperature thereby completing the reaction in a reduced time. Further, use of a high-melting point and high-boiling point starting material makes it possible to separate an optically active alcohol from the reaction mixture with high purity in high yield by means of a simple purification step taking advantage of a difference in physical properties.

8 Claims, No Drawings

PROCESS FOR PRODUCING OPTICALLY ACTIVE ALCOHOL CONTAINING PHENYL GROUP

FIELD OF THE INVENTION

This invention relates to a process for producing an optically active alcohol which is important as an intermediate for synthesis of fine chemicals, such as starting materials or intermediate materials for pharmaceuticals or agricultural chemicals and liquid crystals.

BACKGROUND OF THE INVENTION

Optically active alcohols have been widely used as a starting material or an intermediate for synthesis of fine chemicals, such as pharmaceuticals, agricultural chemicals, and liquid crystalline materials, and various compounds have recently been developed with the increasing demand therefor. For example, there are many useful optically active alcohols containing a phenyl group, such as 1-phenyl-1-ethanol, 1-phenyl-1-pentanol, and 1-(p-chlorophenyl)-1-ethanol. These optically active alcohols are required to have not only high chemical purity but high optical purity in order to exhibit sufficient functions therefrom.

Known purification techniques, such as solvent extraction, fractionation, recrystallization, simple distillation, azeotropic distillation, molecular distillation, and column chromatography, have been utilized for increasing chemical purity of optically active alcohols. On the other hand, increase in optical purity can effectively be achieved by optical resolution of a racemic alcohol using an enzyme (e.g., lipase, lipoprotein lipase, esterase and protease) to recover an optically active enantiomer(s). That is, it is difficult to separate an enantiomer from a racemic alcohol through ordinary chemical reactions accompanied by high temperatures, whereas reactions using an enzyme enables discrimination of enantiomers. Hence, production of optically active alcohols making use of the enzymatic reactions has been studied extensively.

Processes so far proposed for resolving a racemic alcohol using an enzyme to obtain an optically active alcohol include (i) hydrolysis of an ester of a racemic alcohol (see JP-A-1-137996 and JP-A-1-257484, the term "JP-A" as used herein means an "unexamined published Japanese patent application"), (ii) interesterification between a racemic alcohol and a triglyceride (see JP-A-62-166898, and JP-B-6-34752, the term "JP-B" as used herein means an "examined Japanese patent publication"), and (iii) interesterification between an ester of a racemic alcohol and an alcohol (see JP-A-63-173597).

Process (i) entails use of a large quantity of water. Where it is applied to a racemic alcohol ester having high affinity to water, such as a lower 2-alkanol, in an attempt to obtain an optically active alcohol with high purity (inclusive of chemical purity and optical purity, hereunder the same applies), the reaction product must be purified by complicated and expensive means, such as extraction or fractionation using a large amount of a solvent having selective dissolving power for a desired product and/or azeotropic distillation, molecular distillation or preparative liquid chromatography. Moreover, the enzyme tends to be inactivated because of the aqueous system and by-production of, for example, a carboxylic acid. If the enzyme is used in a powder form, it is practically impossible to recover and reuse the enzyme.

According to processes (ii) and (iii), on the other hand, the reaction system has only a trace water content and by-produces no substance causing inactivation of the enzyme so that an operation for extracting and separating a desired compound from an aqueous system as needed in process (i) is not necessary and the enzyme can be recovered and reused. However, in using lipase, for example, since a conventional reaction temperature ranges from about 20° to 70° C. at the broadest and preferably from 20° to 50° C., applicable starting materials are limited to those which are liquid in this temperature range or otherwise must be used in a dissolved state in an organic solvent. In addition, racemic alcohols, particularly those having a substituent of large molecular size, such as a phenyl group, exhibit low reactivity due to steric hindrance of their chemical structure and therefore require a very long time of from several days or even longer for completion of the reaction at such low reaction temperatures as above mentioned.

Where interesterification of process (ii) or (iii) is carried out according to conventional techniques and in the absence of a solvent, starting materials (i.e., racemic alcohols, racemic alcohol esters, triglycerides, alcohols, etc.) which can be used in practice are required to have a melting point approximately equal to or lower than the enzymatic reaction temperature. Accordingly, it is unavoidable to select starting materials having physical properties similar to each other, such as a melting point, a boiling point or solubility in a solvent. Where the reaction of process (iii) is carried out in an organic solvent system (cf. JP-A-63-173597), the alcohol, one of the starting materials, contains 1 to 10 carbon atoms and has a similar melting point to the other starting material, i.e., a racemic alcohol ester. If starting materials having similar physical properties are used, purification means taking advantage of a difference in physical properties among various components can hardly be adopted for efficiently separating and recovering a desired optically active alcohol with increased chemical and optical purity from the interesterification reaction product in which the starting compounds and the reaction product generally provide a complicated equilibrium composition. Therefore, processes (ii) and (iii) as well as process (i) should have a problem that complicated and expensive purification means are necessary.

SUMMARY OF THE INVENTION

In the light of these circumstances, an object of the present invention is to provide a process for producing an optically active alcohol having a phenyl group, in which an enzymatic reaction can be achieved in a reduced time and a desired product can be separated and highly purified through simple and easy operation.

The inventors of the present invention have conducted extensive study for the purpose of overcoming the aforementioned problems and of providing an optically active alcohol having a phenyl group by an industrially simple, easy, and advantageous method. As a result, they have found that interesterification can be completed in a short time to give a reaction mixture from which an optically active alcohol with high purity can easily be isolated in high yield by using, as starting materials, a monoester between a specific racemic alcohol and a fatty acid or a diester between a specific racemic alcohol with a dibasic acid and a specific alcohol and carrying out the reaction in the presence of heat-resistant lipase in a high temperature. The present invention has been reached based on these findings.

The present invention provides:
1. a process for producing an optically active alcohol having a phenyl group comprising the steps of:
   carrying out interesterification between (a) a monoester between a racemic alcohol having a phenyl group and a fatty acid or a diester between a racemic alcohol having a phenyl group and a dibasic acid and (b) an optically inactive non-racemic alcohol having 16 or more carbon atoms in the presence of heat-resistant lipase and in the absence of a solvent under a substantially water-free condition at a temperature of not lower than 81° C. under atmospheric pressure or reduced pressure, and
   separating an optically active alcohol having a phenyl group rich in either one of R- and S-forms from the reaction mixture;
2. the above-mentioned process for producing an optically active alcohol having a phenyl group, wherein the interesterification is carried out under reduced pressure while simultaneously separating an optically active alcohol having a phenyl group rich in either one of R- and S-forms by reduced pressure distillation;
3. the above-mentioned process for producing an optically active alcohol having a phenyl group, wherein the racemic alcohol having a phenyl group is a compound represented by formula (I):

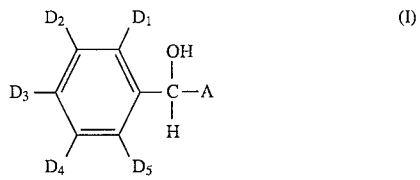

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms; and A represents an alkyl group having 1 to 3 carbon atoms, a trifluoromethyl group or a cyano group;
4. the above-mentioned process for producing an optically active alcohol having a phenyl group, wherein the fatty acid is a straight-chain saturated fatty acid containing 16 or more carbon atoms;
5. the above-mentioned process for producing an optically active alcohol having a phenyl group, wherein the dibasic acid is a straight-chain saturated dibasic acid containing 14 or more carbon atoms;
6. the above-mentioned process for producing an optically active alcohol having a phenyl group, wherein the heat-resistant lipase is a heat-resistant lipase produced by a microorganism belonging to the genus Alcaligenes;
7. the above-mentioned process for producing an optically active alcohol having a phenyl group, wherein the heat-resistant lipase has a powdered form, and at least 90% (as an absolute number) of the heat-resistant lipase has a particle size of from 1 to 100 µm; and
8. the above-mentioned process for producing an optically active alcohol having a phenyl group, wherein the interesterification is carried out at a temperature of from 101° to 120° C.

DETAILED DESCRIPTION OF THE INVENTION

In the present invention, (a) a monoester between a racemic alcohol having a phenyl group (hereinafter referred to as a phenyl-substituted racemic alcohol) and a fatty acid or a diester between a phenyl-substituted racemic alcohol and a dibasic acid and (b) an optically inactive non-racemic alcohol having 16 or more carbon atoms are used as starting materials.

The monoester or diester as starting material (a) can be obtained esterification between a phenyl-substituted racemic alcohol and a fatty acid or a dibasic acid according to known chemical esterification processes. For example, a phenyl-substituted racemic alcohol and a fatty acid or a dibasic acid are esterified in the presence of a catalyst, such as an inorganic acid (e.g., sulfuric acid, hydrochloric acid or p-toluenesulfonic acid), a metal (e.g., zinc, tin or nickel) or an oxide or a chloride of the metal, by heating to 100° to 250° C. while removing by-produced water from the reaction system. If desired, the reaction product is subjected to deacidification treatment with an alkali (e.g., sodium hydroxide or sodium carbonate), decoloration treatment with an adsorbent (e.g., activated carbon or active clay) or deodorizing treatment by adsorption of steam or nitrogen gas under reduced pressure.

The terminology "phenyl-substituted racemic alcohol" as used herein denotes a racemic, straight-chain or branched, and saturated or unsaturated primary or secondary alcohol which is substituted with at least a phenyl group or a phenyl group substituted with a functional group and may further be substituted with a halogen atom (e.g., chlorine, bromine or fluorine), an oxygen atom, a nitrogen atom, a phosphorus atom, a sulfur atom, etc. In particular, compounds represented by formula (I):

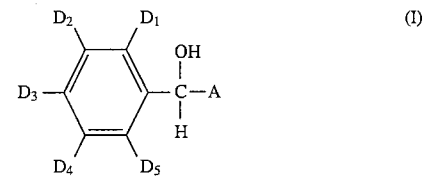

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms; and A represents an alkyl group having 1 to 3 carbon atoms, a trifluoromethyl group or a cyano group, are preferred.

Examples of the phenyl-substituted racemic alcohols are 1-phenyl-1-ethanol, 1-phenyl-1-propanol, 2-phenyl-1-propanol, 1-phenyl-2-propanol, 1-phenyl-1-butanol, 3-phenyl-1-butanol, 2-phenyl-2-butanol, 3-phenyl-2-butanol, 4-phenyl-2-butanol, 1-phenyl-1-pentanol, 4-phenyl-1-pentanol, 2-phenyl-2-pentanol, 3-phenyl-2-pentanol, 4-phenyl-2-pentanol, 5-phenyl-2-pentanol; 1-hexanol having a phenyl group at the 1- or 5-position; 2-hexanol having a phenyl group at any one of the 2- to 6-positions; 1-heptanol having a phenyl group at the 1- or 6-position; 2-heptanol having a phenyl group at any one of the 2- to 7-positions; 1-octanol having a phenyl group at the 1- or 7-positions; 2-octanol having a phenyl group at any one of the 2- to 8-positions; 1-nonanol having a phenyl group at the 1- or 8-positions; 2-nonanol having a phenyl group at any one of the 2- to 9-positions; 1-decanol having a phenyl group at the 1- or 9-positions; 2-decanol having a phenyl group at any one of the 2- to 10-positions; ethyl 3-hydroxy-3-phenylpropionate, 1-phenyl-1,3-propanediol, 2-phenyl-1-cyclohexanol, 1-phenyl-2,2,2-trifluoro-1-ethanol, 1-(2-chlorophenyl)-1-ethanol, 1-(4-chlorophenyl)-1-ethanol, 1-(2,4-dichlorophenyl)-1-ethanol, 1-(2-bromophenyl)-1-ethanol, 1-(4-bromophenyl)-1-ethanol, 1-(2,4-dibromophenyl)-1-ethanol, 1-(2-fluorophenyl)-1-ethanol, 1-(4-fluorophenyl)-1-ethanol, 1-(2,4-difluorophenyl)-1-ethanol, 1-(2-methylphenyl)-1-ethanol, 1-(4-methylphenyl)-1-ethanol, 1-(2,4-dimethylphenyl)-1-ethanol, 1-(2-ethylphenyl)-1-ethanol, 1-(4-ethylphenyl)-1-ethanol, 1-(2,4-diethylphenyl)-1-ethanol, 1-(2-n-propylphenyl)-1-ethanol, 1-(2-methoxyphenyl)-1-ethanol, 1-(2-ethoxyphenyl)-1-ethanol; and the above-mentioned phenyl-substituted 1-propanol, 2-propanol, 1-butanol, 2-butanol, 1-pentanol, 2-pentanol, 1-hexanol, 2-hexanol, 1-heptanol, 2-heptanol, 1-octanol, 2-octanol, 1-nonanol, 2-nonanol, 1-decanol or 2-decanol with its phenyl group replaced with any one of 2-chlorophenyl, 4-chlorophenyl, 2,4-dichlorophenyl, 2-bromophenyl, 4-bromophenyl, 2,4-dibromophenyl, 2-fluorophenyl, 4-fluorophenyl, 2,4-difluorophenyl, 2-methylphenyl, 4-methylphenyl, 2,4-dimethylphenyl, 2-ethylphenyl, 4-ethylphenyl, 2,4-diethylphenyl, 2-n-propylphenyl, 4-n-propylphenyl, 2-methoxyphenyl, 4-methoxyphenyl, 2-ethoxylphenyl and 4-ethoxyphenyl groups. Preferred of them are 1-phenyl-1-ethanol, 1-phenyl-1-propanol, 1-phenyl-1-butanol, 1-phenyl-1-pentanol, 1-(4-chlorophenyl)-1-ethanol, and 1-(2-bromophenyl)-1-ethanol. 1-Phenyl-1-ethanol, 1-phenyl-1-propanol, and 1-(4-chlorophenyl)-1-ethanol are particularly preferred.

The fatty acid can optionally be selected from straight-chain and saturated or unsaturated fatty acids. Examples of suitable fatty acids include n-nonanoic acid, capric acid, lauric acid, n-tridecanoic acid, myristic acid, n-pentadecanoic acid, palmitic acid, n-heptadecanoic acid, palmitoleic acid, stearic acid, oleic acid, elaidic acid, linoleic acid, arachidic acid (20:0), behenic acid (22:0), erucic acid (22:1), lignoceric acid (24:0), cerotic acid (26:0), montanic acid (28:0), melissic acid (30:0), lacceric acid (32:0), and geddic acid (34:0), wherein the figures in the parentheses represent the total carbon atom number:the number of carbon-carbon double bonds in the fatty acid. These fatty acids may be used either individually or as a mixture thereof. In addition, fatty acids obtained from hydrolyzed product of vegetable fats and oils, animal fats and oils and fish oils; hydrogenation products of fatty acids obtained by hydrolysis of these fats and oils; and higher or long chain fatty acids separated from hydrolyzed products of waxes, such as montan wax, carnauba wax, rice wax, candelilla wax, sunflower wax, bees wax, whale wax, shellac wax, insect wax, sugar cane wax, poppy seed wax, and cotton wax.

The dibasic acid can optionally be selected from straight-chain or branched and saturated dibasic acids. Examples of suitable dibasic acids are dodecamethylenedicarboxylic acid, tetradecamethylenedicarboxylic acid, hexadecamethylenedicarboxylic acid, heptadecamethylenedicarboxylic acid, octadecamethylenedicarboxylic acid, nonadecamethylenedicarboxylic acid, eicosamethylenedicarboxylic acid, docosamethylenedicarboxylic acid, tetracosamethylenedicarboxylic acid, hexacosamethylenedicarboxylic acid, octacosamethylenedicarboxylic acid, and a dimer acid derived from oleic acid, erucic acid, etc. These dibasic acids may be used either individually or as a mixture thereof. In addition, long chain dibasic acids separated from Japan wax or sediment of crude sesame oil may also be used.

Since the upper limit of the temperature of the interesterification reaction according to the present invention is 130° C. as hereinafter described, the above-described racemic alcohol and fatty acid or dibasic acid to be combined with each other should be selected so that the mono- or diester formed therefrom may be liquid at a temperature at which interesterification reaction is carried out. Further, from the standpoint of convenience in the purification step for separating a desired optically active alcohol from the reaction mixture, the fatty acid is desirably a straight-chain saturated fatty acid having 16 or more, preferably 18 to 30, still preferably 20 to 28, most preferably 22 to 28, carbon atoms. Where a fatty acid containing less than 16 carbon atoms or a branched fatty acid is used, the tendency of requiring strictness of the purification conditions for isolating a desired optically active alcohol with high purity in high yield would be increased. Fatty acids containing more than 34 carbon atoms are not easily available on an industrial scale. The fatty acid monoesters to be used in the present invention preferably have a high melting point, i.e., not less than 60° C., most preferably not less than 70° C.

The dibasic acid is desirably a straight-chain saturated dibasic acid having 14 or more, preferably 16 to 30, still preferably 18 to 28, most preferably 20 to 28, carbon atoms. Where a dibasic acid containing less than 14 carbon atoms or an unsaturated dibasic acid is used, the tendency of requiring strictness of the purification conditions for isolating a desired optically active alcohol with high purity in high yield would be increased. Dibasic acids containing more than 45 carbon atoms are not easily available on an industrial scale. The dibasic acid diesters to be used in the present invention preferably have a high melting point, i.e., not less than 60° C., more preferably not less than 70° C.

The optically inactive non-racemic alcohol having 16 or more carbon atoms which can be used in the present invention as starting material (b) include 1-hexadecanol (cetanol), 1-heptadecanol, 1-octadecanol (stearyl alcohol), 2-heptylundecanol (isostearyl alcohol), oleyl alcohol, 1-eicosanol, 1-docosanol (behenyl alcohol), 1-tricosanol, 1-tetracosanol, 1-pentacosanol, 1-hexacosanol, 1-heptacosanol, 1-octacosanol, 1-nonacosanol, melissyl alcohol ($C_{30}$), hentriacontanol ($C_{31}$), and laccerol ($C_{32}$). Among these alcohols, straight-chain saturated alcohols having 16 to 30 carbon atoms, more preferably 18 to 28 carbon atoms are preferable. Where an alcohol having less than 16 carbon atoms is used, a desired optically active alcohol is difficult to separate in the purification step, and those having more than 34 carbon atoms are not easily available on an industrial scale.

The interesterification reaction of the present invention is characterized by using heat-resistant lipase is used. Therefore, according to the present invention, the starting materials (a) and (b) can be maintained in a liquid state, there is no need to use a solvent for the starting materials as has been required in the conventional processes, the reaction proceeds rapidly, and use of a high-melting point ester and a high-melting point alcohol can be used thereby making it easy to separate and purify an optically active alcohol.

The terminology "heat-resistant lipase" as used herein means lipase species which are capable of catalyzing interesterification at a temperature of 81° C. or higher. Such heat-resistant lipase include lipase PL-266 produced by Alcaligenes sp. PL-266 (FERM P-3187) disclosed in JP-B-58-36953, which is available as Lipase QL produced by Meito Sangyo Co., Ltd.; lipase PL-679 produced by Alcaligenes sp. PL-679 (FERM P-3783) disclosed in JP-B-60-15312, which is available as Lipase PL produced by Meito Sangyo Co., Ltd.; and lipase of *Rhizopus chinensis* described in JP-A-59-156282. The first two of them are preferred. In carrying out the present invention, Lipase QL and Lipase PL, both originated in Alcaligenes sp. and produced by Meito Sangyo Co., Ltd., are convenient for use. Lipase QL is especially preferred. Heat-resistant lipase may be used as immobilized on a known carrier, such as activated carbon, Celite, adsorbing resins, ion-exchange resins, glass beads, or ceramics (cf. Ripaze sonokiso to oyo (Lipase, Fundamentals and Application), pp. 336–343, 1991, published by Saiwai Syobo), but is preferably added to the starting materials in the form of powder as hereinafter described.

Phenyl-substituted racemic alcohol monoester or diester (a) and alcohol (b) are used at an (a):(b) molar ratio of 1:≦5, preferably form 1:3 to 1:5. The interesterification reaction can be carried out by dispersing heat-resistant lipase, preferably heat-resistant lipase of powder form, in a substantially water-free reaction system comprising the mixture of starting materials (a) and (b) and containing no organic solvent for dissolving the starting materials while stirring or shaking. The term "substantially water-free" as used herein means that the water content of the reaction system should be not more than about 0.1% by weight, which is an equivalent water content of the starting materials, preferably not more than 0.05% by weight (hereinafter the same applies). It is desirable to carry out interesterification with the particle size of the lipase powder being controlled in such a manner that not less than 90% (as an absolute number) of the lipase particles have a particle size in the range of from 1 to 100 µm, preferably from 20 to 50 µm. Such a particle size distribution can be obtained by dispersing heat-resistant lipase powder in the starting material mixture (melted by heating if desired) and subjecting the dispersion to ultrasonication, filtration using a precision membrane or an ultrafiltration membrane, centrifugal sedimentation, and the like. Preferably, ultrasonication under conditions of 20 to 150 kHz and 100 to 250 W for 1 to 30 minutes would be convenient.

The reaction temperature is set at 81° C. or higher, preferably from 91° to 130° C., still preferably from 101° to 120° C., and the reaction is performed under atmospheric pressure or reduced pressure with mild stirring or shaking for a prescribed period of time, preferably several to 100 hours, while monitoring the reaction rate by, for example, gas chromatography. If the reaction temperature is lower than 81° C., the reaction progress is slow. Temperatures exceeding 130° C. tend to inactivate the lipase even it is heat resistant.

In a preferred embodiment of the present invention, interesterification is carried out under reduced pressure, preferably under a pressure of 1 to 5 mmHg, with the other conditions being the same as those described above, so that the optically active alcohol produced and released in the reaction system may be recovered by vacuum distillation simultaneously with the progress of the interesterification reaction. In this embodiment, the interesterification reaction rapidly proceeds.

As shown in the following reaction schemes (II) or (III), the interesterification reaction according to the present invention consists of so-called alcoholysis of a racemic alcohol mono- or diester with an optically inactive and non-racemic alcohol. Accordingly, the resulting reaction mixture is a composition comprising various components, including a released optically active alcohol having either one of R- and S-forms, a produced fatty acid monoester or dibasic acid diester of the optically inactive and non-racemic alcohol, and an unreacted fatty acid monoester or dibasic acid diester of an optically active alcohol having either one of R- and S-forms. The reaction mixture also contains the unreacted starting materials.

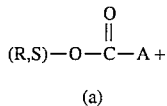

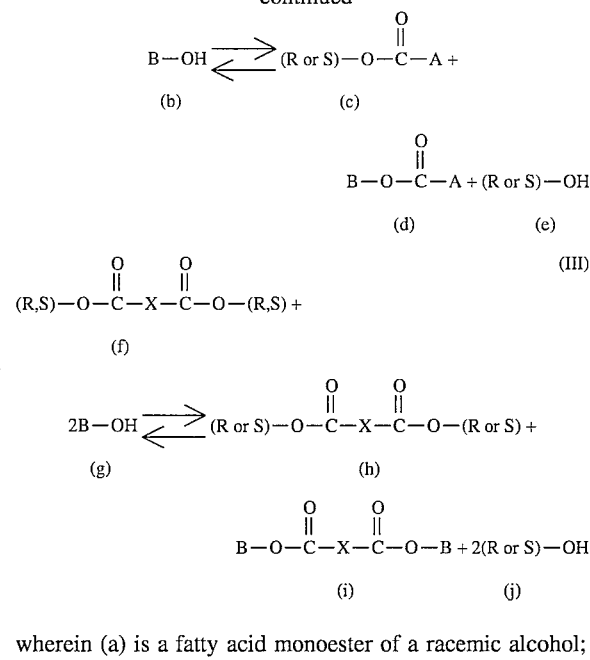

wherein (a) is a fatty acid monoester of a racemic alcohol; (b) is an optically inactive non-racemic alcohol; (c) a fatty acid monoester of an optically active alcohol; (d) a fatty acid monoester of an optically inactive non-racemic alcohol; (e) is an optically active alcohol; (f) is a dibasic acid diester of a racemic alcohol; (g) is an optically inactive non-racemic alcohol; (h) is a dibasic acid diester of an optically active alcohol; (i) is a dibasic acid diester of an optically inactive non-racemic alcohol; and (j) is an optically active alcohol.

In the reaction mixture obtained by conventional processes, these components have similar physical properties and, therefore, complicated purification steps have been required for recovery of a desired optically active alcohol. To the contrary, the present invention is characterized by starting with an optically inactive non-racemic alcohol having 16 or more carbon atoms, whose physical properties (melting point, boiling point, solubility to solvents, etc.) are greatly different from those of the racemic alcohol, thus making it easy to isolate a desired optically active alcohol.

More specifically, a highly pure optically active alcohol can be isolated in high yield by first removing lipase powder by means of a precision filtration membrane, such as filter paper, and subjecting the filtrate to a relatively simple purification step, such as vacuum distillation, fractionation with or without a solvent, recrystallization, silica gel column chromatography, and so on, suitably vacuum distillation alone.

Further, where the interesterification is conducted under reduced pressure, a desired optically active alcohol having either one of R- and S-forms can easily be distilled off under reduced pressure apart from other components in the reaction system. By this separation, the reaction equilibrium is shifted toward the right hand side (the side of the reaction product) in the above-illustrated reaction schemes, whereby the reaction is further accelerated, resulting in the formation of highly pure optically active alcohol in a higher yield.

The unreacted enantiomer remaining in the form of a mono- or diester can be separated from the residual reaction mixture by any known technique, such as column chromatography, and then hydrolyzed with an acid (e.g., hydrochloric acid or sulfuric acid) or an alkali (e.g., sodium hydroxide or potassium hydroxide) to isolate the corresponding optically active alcohol with high purity in the same manner. The heat-resistant lipase used in the reaction can be recovered and reused in the same interesterification reaction.

The present invention will now be illustrated in greater detail with reference to Examples, but it should be understood that the present invention is not construed as being limited thereto. The chemical purity of the compounds obtained in Examples and Comparative Examples was determined by gas chromatography using GC-14A manufactured by Shimadzu Corp. The optical purity of the compounds was determined by measuring the specific rotation with a polarimeter DIP-370 manufactured by Nippon Bunko K.K. and comparing the measured value with that of a standard preparation.

EXAMPLE 1

In a 500 ml separable flask were put 10 g of Lipase QL of Alcaligenes sp. origin (a product of Meito Sangyo Co., Ltd., hereinafter the same applies), 150 g of stearic acid monoester of (R,S)-1-phenyl-1-ethanol, and 300 g of stearyl alcohol, and the mixture was subjected to ultrasonication using ultrasonic wave generating equipment SUS-103 manufactured by Shimadzu Corp. at 80° C. and 45 kHz for 1 minute. The mixture was stirred at 95° C. and 350 rpm under atmospheric pressure for 24 hours to conduct interesterification. The water content of the reaction system was 0.04% by weight as measured by Karl Fischer's method (hereinafter the same applies), and 95% or more of the lipase particles had a particle size of 30 to 70 μm as measured with a particle size distribution measuring apparatus Multisizer manufactured by Coulter Electronics Inc. (hereinafter the same applies). After completion of the reaction, gas chromatographic analysis of the reaction mixture revealed that 49 mol % of the stearic acid monoester of (R,S)-1-phenyl-1-ethanol had undergone interesterification. Lipase was removed using a membrane filter (0.5 μm) (produced by Advantec Co., hereinafter the same applies), and the filtrate was distilled at 90° C. and 3 mmHg to give (R)-1-phenyl-1-ethanol (yield; 91%: chemical purity: 99% or higher; optical purity: 99% ee). On the other hand, the residual stearic acid monoester of 1-phenyl-1ethanol was separated from the residue by silica gel column chromatography and alkali-hydrolyzed to recover (S)-1-phenyl-1-ethanol (yield: 88%; chemical purity: 99% or higher; optical purity: 99% ee or higher).

EXAMPLE 2

In a 500 ml separable flask were put 10 g of Lipase PL of Alcaligenes sp. origin (produced by Meito Sangyo Co., Ltd., hereinafter the same applies), 130 g of palmitic acid ester of (R,S)-1-(p-chlorophenyl)-1-ethanol, and 320 g of n-hexadecanol. After the same ultrasonication as in Example 1, the mixture was subjected to interesterification by stirring at 85° C. and 350 rpm under atmospheric pressure for 24 hours. The water content of the reaction system was 0.05% by weight, and 90% of the lipase particles had a particle size of 20 to 60 μm. After completion of the reaction, gas chromatographic analysis of the reaction mixture revealed interesterification of 49 mol % of the palmitic monoester of (R,S)-1-(p-chlorophenyl)-1-ethanol. Lipase was removed by filtration using the membrane filter (0.5 μm), and the filtrate was subjected to distillation at 95° C. and 3 mmHg to recover (R)-1-(p-chlorophenyl)-1-ethanol (yield: 92%; chemical purity: 99% or higher; optical purity: 99% ee or higher). On the other hand, the residual palmitic acid monoester of 1-(p-chlorophenyl)-1-ethanol was separated from the residue by silica gel column chromatography and alkali-hydrolyzed to recover (S)-1-(p-chlorophenyl)-1-ethanol (yield: 85%; chemical purity: 99% or higher; optical purity: 99% ee or higher).

EXAMPLE 3

In a 500 ml separable flask were put 15 g of Lipase QL, 120 g of montanic acid monoester of (R,S)-2-(2,4-difluorophenyl)-2-octanol, and 340 g of behenyl alcohol. After the same ultrasonication as in Example 1, the mixture was subjected to interesterification by stirring at 110° C. and 250 rpm under atmospheric pressure for 20 hours. The water content of the reaction system was 0.01% by weight, and 93% of the lipase particles had a particle size of 30 to 60 μm. After completion of the reaction, gas chromatographic analysis of the reaction mixture revealed interesterification of 50 mol % of the montanic acid monoester of (R,S)-2-(2, 4-difluorophenyl)-2-octanol. Lipase was removed by filtration using the membrane filter (0.5 μm), and the filtrate was subjected to distillation at 110° C. and 2 mmHg to recover (R)-2-(2,4-difluorophenyl)-2-octanol (yield: 90%; chemical purity: 99%; optical purity: 99% ee). On the other hand, the residual montanic acid monoester of 2-(2,4-difluorophenyl)-2-octanol was separated from the residue by silica gel column chromatography and alkali-hydrolyzed to recover (S)-2-(2,4-difluorophenyl)-2-octanol (yield: 88%; chemical purity: 99% or higher; optical purity: 99% ee or higher).

EXAMPLE 4

In a 500 ml separable flask were put 10 g of Lipase QL, 150 g of oleic acid monoester of (R,S)-1-phenyl-1-propanol, and 300 g of stearyl alcohol. After the same ultrasonication as in Example 1, the mixture was subjected to interesterification by stirring at 105° C. and 300 rpm under atmospheric pressure for 23 hours. The water content of the reaction system was 0.01% by weight, and 95% of the lipase particles had a particle size of 20 to 50 μm. After completion of the reaction, gas chromatographic analysis of the reaction mixture revealed interesterification of 49 mol % of the oleic acid monoester of (R,S)-1-phenyl-1-propanol. Lipase was removed by filtration using the membrane filter (0.5 μm), and the filtrate was subjected to distillation at 95° C. and 2 mmHg to recover (R)-1-phenyl-1-propanol (yield: 92%; chemical purity: 100%; optical purity: 100% ee). On the other hand, the residual oleic acid monoester of 1-phenyl-1-propanol was separated from the residue by silica gel column chromatography and alkali-hydrolyzed to recover (S)-1-phenyl-1-propanol (yield: 89%; chemical purity: 99% or higher; optical purity: 99% ee or higher).

COMPARATIVE EXAMPLE 1

Interesterification and following procedures were carried out in the same manner as in Example 2, except for replacing 320 g of n-hexadecanol with 300 g of myristyl alcohol. As a result, (R)-1-(p-chlorophenyl)-1-ethanol was separated in a yield of 97% with a chemical purity of 95% and an optical purity of 92% ee and (S)-1-(p-chlorophenyl)-1-ethanol was separated in a yield of 82% with a chemical purity of 93% and an optical purity of 90% ee.

EXAMPLE 5

In a 500 ml separable flask were put 10 g of Lipase PL, 100 g of 1,14-tetradecadicarboxylic acid (dodecamethylenedicarboxylic acid) diester of (R,S)-1-phenyl-1-ethanol, and 300 g of oleyl alcohol. After the same ultrasonication as in Example 1, the mixture was subjected to interesterification by stirring at 85° C. and 350 rpm under atmospheric pressure for 48 hours. The water content of the reaction system was 0.03% by weight, and 95% or more of the lipase particles had a particle size of 30 to 70 µm. After completion of the reaction, gas chromatographic analysis of the reaction mixture revealed that 50 mol % of the 1,14-tetradecadicarboxylic acid diester of (R,S)-1-phenyl-1-ethanol had undergone interesterification. Lipase was removed by filtration using the membrane filter (0.5 µm), and the filtrate was subjected to distillation at 90° C. and 3 mmHg to recover (R)-1-phenyl-1-ethanol (yield: 90%; chemical purity: 100%; optical purity: 100% ee). On the other hand, the residual 1,14-tetradecadicarboxylic acid diester of 1-phenyl-1-ethanol was separated from the residue by silica gel column chromatography and alkali-hydrolyzed to recover (S)-1-phenyl-1-ethanol (yield: 95%; chemical purity: 100%; optical purity: 100% ee).

EXAMPLE 6

In a 500 ml separable flask were put 10 g of Lipase QL, 100 g of 1,20-eicosadicarboxylic acid (octadecamethylenedicarboxylic acid) diester of (R,S)-1-phenyl-1-propanol, and 300 g of stearyl alcohol. After the mixture was subjected to ultrasonication in the same manner as in Example 1 but at 105° C., the mixture was stirred at 105° C. and 350 rpm under atmospheric pressure for 24 hours to conduct interesterification. The water content of the reaction system was 0.05% by weight, and 95% or more of the lipase particles had a particle size of 20 to 60 µm. After completion of the reaction, gas chromatographic analysis of the reaction mixture revealed that 49 mol % of the 1,20-eicosadicarboxylic acid diester of (R,S)-1-phenyl-1-propanol had undergone interesterification. Lipase was removed by filtration using the membrane filter (0.5 µm), and the filtrate was subjected to distillation at 95° C. and 2 mmHg to recover (R)-1-phenyl-1-propanol (yield: 90%; chemical purity: 100%; optical purity: 99% ee or higher). On the other hand, the residual 1,20-eicosadicarboxylic acid diester of 1-phenyl-1-propanol was separated from the residue by silica gel column chromatography and alkali-hydrolyzed to recover (S)-1-phenyl-1-propanol (yield: 92%; chemical purity: 100%; optical purity: 99% ee or higher).

EXAMPLE 7

In a 500 ml separable flask were put 10 g of Lipase QL, 100 g of a 1,28-octacosadicarboxylic acid (hexacosamethylenedicarboxylic acid) diester of (R,S)-2-(2,4-difluorophenyl)-2-octanol, and 330 g of behenyl alcohol. After the same ultrasonication as in Example 1, the mixture was subjected to interesterification by stirring at 110° C. and 250 rpm under atmospheric pressure for 20 hours. The water content of the reaction system was 0.02% by weight, and 95% of the lipase particles had a particle size of 20 to 50 µm. After completion of the reaction, gas chromatographic analysis of the reaction mixture revealed that 50 mol % of the 1,28-octacosadicarboxylic acid diester of (R,S)-2-(2,4-difluorophenyl)-2-octanol had undergone interesterification. Lipase was removed by filtration using the membrane filter (0.5 µm), and the filtrate was subjected to distillation at 95° C. and 2 mmHg to recover (R)-2-(2,4-difluorophenyl)-2-octanol (yield: 93%; chemical purity: 99%; optical purity: 100% ee). On the other hand, the residual 1,28-octacosadicarboxylic acid diester of 2-(2,4-difluorophenyl)-2-octanol was separated from the residue by silica gel column chromatography and alkali-hydrolyzed to recover (S)-2-(2,4-difluorophenyl)-2-octanol (yield: 93%; chemical purity: 100%; optical purity: 100% ee).

EXAMPLE 8

In a 500 ml separable flask were put 15 g of Lipase QL, 100 g of a 1,20-eicosadicarboxylic acid (octadecamethylenedicarboxylic acid) diester of (R,S)-1-(p-chlorophenyl)-1-ethanol, and 320 g of n-hexadecanol. After the same ultrasonication as in Example 1, the mixture was subjected to interesterification by stirring at 103° C. and 350 rpm under atmospheric pressure for 25 hours. The water content of the reaction system was 0.03% by weight, and 95% or more of the lipase particles had a particle size of 20 to 60 µm. After completion of the reaction, gas chromatographic analysis of the reaction mixture revealed that 50 mol % of the 1,20-eicosadicarboxylic acid diester of (R,S)-1-(p-chlorophenyl)-1-ethanol had undergone interesterification. Lipase was removed by filtration using the membrane filter (0.5 µm), and the filtrate was subjected to distillation at 95° C. and 3 mmHg to recover (R)-1-(p-chlorophenyl)-1-ethanol (yield: 95%; chemical purity: 99% or higher; optical purity: 100% ee). On the other hand, the residual 1,20-eicosadicarboxylic acid diester of 1-(p-chlorophenyl)-1-ethanol was separated from the residue by silica gel column chromatography and alkali-hydrolyzed to recover (S)-1-(p-chlorophenyl)-1-ethanol (yield: 87%; chemical purity: 99%; optical purity: 100% ee).

COMPARATIVE EXAMPLE 2

Interesterification and following procedures were carried out in the same manner as in Example 8, except for replacing 320 g of n-hexadecanol with 300 g of myristyl alcohol. As a result, (R)-1-(p-chlorophenyl)-1-ethanol in a yield of 93% was separated with a chemical purity of 95% and an optical purity of 93% ee and (S)-1-(p-chlorophenyl)-1-ethanol was separated in a yield of 81% with a chemical purity of 93% and an optical purity of 91% ee.

EXAMPLE 9

In a 500 ml separable flask were put 10 g of Lipase QL, 150 g of stearic acid monoester of (R,S)-1-phenyl-1-ethanol, and 300 g of stearyl alcohol. After the same ultrasonication as in Example 1, the mixture was subjected to interesterification by stirring at 95° C. and 350 rpm under reduced pressure of 5 mmHg for 12 hours while collecting the distillate. The water content of the reaction system was 0.05% by weight, and 95% or more of the lipase particles had a particle size of 30 to 70 µm. The gas chromatographic analysis of the distillate revealed that 49 mol % of the stearic acid monoester of (R,S)-1-phenyl-1-ethanol had undergone interesterification, and (R)-1-phenyl-1-ethanol was obtained (yield: 95%; chemical purity: 99% or more; optical purity: 99%). After completion of the reaction, lipase was removed from the reaction mixture by filtration using the membrane filter (0.5 µm), and the residual stearic acid monoester of 1-phenyl-1-ethanol was separated from the filtrate by silica gel column chromatography and alkali-hydrolyzed to recover (S)-1-phenyl-1-ethanol (yield: 93%; chemical purity: 99% or more; optical purity: 99% ee).

EXAMPLE 10

In a 500 ml separable flask were put 10 g of Lipase PL, 130 g of palmitic acid monoester of (R,S)-1-(p-chlorophenyl)-1-ethanol, and 320 g of n-hexadecanol. After the same ultrasonication as in Example 1, the mixture was subjected to interesterification by stirring at 85° C. and 350 rpm under reduced pressure of 2 mmHg for 18 hours while collecting the distillate. The water content of the reaction system was 0.02% by weight, and 93% or more of the lipase particles had a particle size of 20 to 70 µm. The gas chromatographic analysis of the collected distillate revealed that 49 mol % of the palmitic acid monoester of (R,S)-1-(p-chlorophenyl)-1-ethanol had undergone interesterification, and (R)-1-(p-chlorophenyl)-1-ethanol was obtained (yield: 93%; chemical purity: 99% or more; optical purity: 99% or more). After completion of the reaction, lipase was removed from the reaction mixture by filtration using the membrane filter (0.5 µm), and the residual palmitic acid monoester of 1-(p-chlorophenyl)-1-ethanol was separated from the filtrate by silica gel column chromatography and alkali-hydrolyzed to recover (S)-1-(p-chlorophenyl)-1-ethanol (yield: 90%; chemical purity: 99% or more; optical purity: 99% ee).

EXAMPLE 11

In a 500 ml separable flask were put 15 g of Lipase QL, 100 g of montanic acid monoester of (R,S)-2-(2,4-difluorophenyl)-2-octanol, and 300 g of behenyl alcohol. After the same ultrasonication as in Example 1, the mixture was subjected to interesterification by stirring at 110° C. and 200 rpm under reduced pressure of 3 mmHg for 18 hours while collecting the distillate. The water content of the reaction system was 0.01% by weight, and 95% of the lipase particles had a particle size of 20 to 50 µm. The gas chromatographic analysis of the collected distillate revealed that 49 mol % of the montanic acid monoester of (R,S)-2-(2,4-difluorophenyl)-2-octanol had undergone interesterification, and (R)-2-(2,4-difluorophenyl)-2-octanol was obtained (yield: 94%; chemical purity: 99%; optical purity: 99% ee or more). After completion of the reaction, lipase was removed from the reaction mixture by filtration using the membrane filter (0.5 µm), and the residual montanic acid monoester of 2-(2,4-difluorophenyl)-2-octanol was separated from the filtrate by silica gel column chromatography and alkali hydrolyzed to recover (S)-2-(2,4-difluorophenyl)-2-octanol (yield: 97%; chemical purity: 100%; optical purity: 100% ee).

EXAMPLE 12

In a 500 ml separable flask were put 10 g of Lipase QL, 150 g of oleic acid monoester of (R,S)-1-phenyl-1-propanol, and 300 g of stearyl alcohol. After the ultrasonication, the mixture was subjected to interesterification by stirring at 105° C. and 300 rpm under reduced pressure of 2 mmHg for 20 hours while collecting the distillate. The water content of the reaction system was 0.01% by weight, and 95% or more of the lipase particles had a particle size of 30 to 50 µm. The gas chromatographic analysis of the collected distillate revealed that 50 mol % of the oleic acid monoester of (R,S)-1-phenyl-1-propanol had undergone interesterification, and (R)-1-phenyl-1-propanol was obtained (yield: 97%; chemical purity: 100%; optical purity: 100% ee). After completion of the reaction, lipase was removed from the reaction mixture by filtration using the membrane filter (0.5 µm), and the residual oleic acid monoester of 1-phenyl-1-propanol was separated from the filtrate by silica gel column chromatography and alkali-hydrolyzed to recover (S)-1-phenyl-1-propanol (yield: 95%; chemical purity: 100%; optical purity: 99% ee or higher).

COMPARATIVE EXAMPLE 3

Interesterification and following procedures were carried out in the same manner as in Example 10, except for replacing 320 g of n-hexadecanol with 300 g of myristyl alcohol. As a result, there were separated (R)-1-(p-chlorophenyl)-1-ethanol in a yield of 90% with a chemical purity of 90% and an optical purity of 84% ee and (S)-1-(p-chlorophenyl)-1-ethanol in a yield of 78% with a chemical purity of 91% and an optical purity of 83% ee.

EXAMPLE 13

In a 500 ml separable flask were put 10 g of Lipase PL, 100 g of 1,14-tetradecadicarboxylic acid (dodecamethylenedicarboxylic acid) diester of (R,S)-1-phenyl-1-ethanol, and 300 g of oleyl alcohol. The mixture was subjected to ultrasonication in the same manner as in Example 1 but at 85° C. and then subjected to interesterification by stirring at 85° C. and 350 rpm under reduced pressure of 5 mmHg for 27 hours while collecting the distillate. The water content of the reaction system was 0.04% by weight, and 95% or more of the lipase particles had a particle size of 30 to 60 µm. After completion of the reaction, gas chromatographic analysis of the distillate revealed that 50 mol % of the 1,14-tetradecadicarboxylic acid diester of (R,S)-1-phenyl-1-ethanol had undergone interesterification, and (R)-1-phenyl-1-propanol was obtained (yield: 93%; chemical purity: 100%; optical purity: 100% ee). After completion of the reaction, lipase was removed from the reaction mixture by filtration using the membrane filter (0.5 µm), and the residual 1,14-tetradecadicarboxylic acid diester of 1-phenyl-1-ethanol was separated from the filtrate by silica gel column chromatography and alkali-hydrolyzed to recover (S)-1-phenyl-1-ethanol (yield: 95%; chemical purity: 100%; optical purity: 100% ee).

EXAMPLE 14

In a 500 ml separable flask were put 10 g of Lipase QL, 100 g of 1,20-eicosadicarboxylic acid (octadecamethylenedicarboxylic acid) diester of (R,S)-1-phenyl-1-propanol, and 300 g of stearyl alcohol. The mixture was subjected to ultrasonication in the same manner as in Example 1 but at 105° C. and then subjected to interesterification by stirring at 105° C. and 350 rpm under reduced pressure of 3 mmHg for 12 hours while collecting the distillate. The water content of the reaction system was 0.03% by weight, and 95% of the lipase particles had a particle size of 20 to 70 µm. After completion of the reaction, gas chromatographic analysis of the distillate revealed that 49 mol % of the 1,20-eicosadicarboxylic acid diester of (R,S)-1-phenyl-1-propanol had undergone interesterification, and (R)-1-phenyl-1-propanol was obtained (yield: 97%; chemical purity: 100%; optical purity: 99% ee or higher). After completion of the reaction, lipase was removed from the reaction mixture by filtration using the membrane filter (0.5 µm), and the residual 1,20-eicosadicarboxylic acid diester of 1-phenyl-1-propanol was separated from the filtrate by silica gel column chromatography and alkali-hydrolyzed to recover (S)-1-phenyl-1-propanol (yield: 98%; chemical purity: 100%; optical purity: 99% ee or higher).

EXAMPLE 15

In a 500 ml separable flask were put 10 g of Lipase QL, 100 g of 1,28-octacosadicarboxylic acid (hexacosamethylenedicarboxylic acid) diester of (R,S)-2-(2,4-difluorophenyl)-2-octanol, and 330 g of behenyl alcohol. After the same ultrasonication as in Example 13, the mixture was subjected to interesterification by stirring at 110° C. and 300 rpm under reduced pressure of 3 mmHg for 19 hours while collecting the distillate. The water content of the reaction system was 0.01% by weight, and 95% or more of the lipase particles had a particle size of 20 to 50 µm. The gas chromatographic analysis of the collected distillate revealed that 50 mol % of the 1,28-octacosadicarboxylic acid diester of (R,S)-2-(2,4-difluorophenyl)-2-octanol had undergone interesterification, and (R)-2-(2,4-difluorophenyl)-2-octanol was obtained (yield: 95%; chemical purity: 99% or higher; optical purity: 99% ee). After completion of the reaction, lipase was removed from the reaction mixture by filtration using the membrane filter (0.5 µm), and the residual 1,28-octacosadicarboxylic acid diester of 2-(2,4-difluorophenyl)-2-octanol was separated from the filtrate by silica gel column chromatography and alkali-hydrolyzed to recover (S)-2-(2,4-difluorophenyl)-2-octanol (yield: 94%; chemical purity: 100%; optical purity: 100% ee).

EXAMPLE 16

In a 500 ml separable flask were put 15 g of Lipase QL, 100 g of 1,20-eicosadicarboxylic acid (octadecamethylenedicarboxylic acid) diester of (R,S)-1-(p-chlorophenyl)-1-ethanol, and 320 g of n-hexadecanol. After the same ultrasonication as in Example 13, the mixture was subjected to interesterification by stirring at 103° C. and 250 rpm under reduced pressure of 5 mmHg for 24 hours while collecting the distillate. The water content of the reaction system was 0.02% by weight, and 95% or more of the lipase particles had a particle size of 20 to 50 µm. The gas chromatographic analysis of the collected distillate revealed that 49 mol % of the 1,20-eicosadicarboxylic acid diester of (R,S)-1-(p-chlorophenyl)-1-ethanol had undergone interesterification, and (R)-1-(p-chlorophenyl)-1-ethanol was obtained (yield: 97%; chemical purity: 100%; optical purity: 100% ee). After completion of the reaction, lipase was removed from the reaction mixture by filtration using the membrane filter (0.5 µm), and the residual 1,20-eicosadicarboxylic acid diester of 1-(p-chlorophenyl)-1-ethanol was separated from the filtrate by silica gel column chromatography and alkali-hydrolyzed to recover (S)-1-(p-chlorophenyl)-1-ethanol (yield: 95%; chemical purity: 100%; optical purity: 100% ee).

COMPARATIVE EXAMPLE 4

Interesterification and following procedures were carried out in the same manner as in Example 16, except for replacing 320 g of n-hexadecanol with 300 g of myristyl alcohol. As a result, (R)-1-(p-chlorophenyl)-1-ethanol was separated in a yield of 92% with a chemical purity of 93% and an optical purity of 90% ee and (S)-1-(p-chlorophenyl)-1-ethanol was separated in a yield of 81% with a chemical purity of 91% and an optical purity of 89% ee.

According to the present invention, since optical resolution of a phenyl-substituted racemic alcohol ester is effected by using heat-resistant lipase, there is no need to use a solvent for the starting materials, and high-melting materials can be used, thereby making it possible to perform interesterification at a high temperature that has conventionally been impossible and to complete the reaction in a reduced time. Further, since a high-melting and high-boiling long chain alcohol can be used as a starting material, an optically active alcohol having either one of R- and S-forms can easily be separated with high purity in high yield from the reaction mixture by means of a simple purification step taking advantage of a difference in physical properties. In particular, where the interesterification is carried out under reduced pressure, separation and purification of an optically active alcohol can be conducted simultaneously with the reaction progress. Further, the other optically active alcohol having an R- or S-form can easily be isolated with high purity.

While the invention has been described in detail and with reference to specific examples thereof, it will be apparent to one skilled in the art that various changes and modifications can be made therein without departing from the spirit and scope thereof.

What is claimed is:

1. A process for producing an optically active alcohol having a phenyl group comprising the steps of:

carrying out interesterification between (a) a monoester between a racemic alcohol having a phenyl group and a fatty acid or a diester between a racemic alcohol having a phenyl group and a dibasic acid and (b) an optically inactive non-racemic alcohol having 16 or more carbon atoms in the presence of heat-resistant lipase and in the absence of a solvent under a substantially water-free condition at a temperature of not lower than 81° C. under atmospheric pressure or reduced pressure, and separating an optically active alcohol having a phenyl group rich in either one of R- and S-forms from the reaction mixture.

2. A process for producing an optically active alcohol having a phenyl group according to claim 1, wherein said interesterification is carried out under reduced pressure while simultaneously separating an optically active alcohol having a phenyl group rich in either one of R- and S-forms by vacuum distillation.

3. A process for producing an optically active alcohol having a phenyl group according to claim 1 or 2, wherein said racemic alcohol having a phenyl group is a compound represented by formula (I):

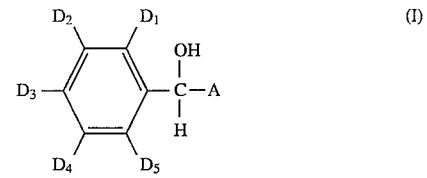

wherein $D_1$, $D_2$, $D_3$, $D_4$, and $D_5$ each represent a hydrogen atom, a halogen atom, an alkyl group having 1 to 3 carbon atoms or an alkoxy group having 1 to 3 carbon atoms; and A represents an alkyl group having 1 to 3 carbon atoms, a trifluoromethyl group or a cyano group.

4. A process for producing an optically active alcohol having a phenyl group according to claim 1 or 2, wherein said fatty acid is a straight-chain saturated fatty acid containing 16 or more carbon atoms.

5. A process for producing an optically active alcohol having a phenyl group according to claim 1 or 2, wherein said dibasic acid is a straight-chain saturated dibasic acid containing 14 or more carbon atoms.

6. A process for producing an optically active alcohol having a phenyl group according to claim 1 or 2, wherein said heat-resistant lipase is a heat-resistant lipase produced by a microorganism belonging to the genus Alcaligenes.

7. A process for producing an optically active alcohol having a phenyl group according to claim 1 or 2, wherein said heat-resistant lipase has a powdered form, and at least 90% (as an absolute number) of said heat-resistant lipase has a particle size of from 1 to 100 µm.

8. A process for producing an optically active alcohol having a phenyl group according to claim 1 or 2, wherein said interesterification is carried out at a temperature of from 101° to 120° C.

* * * * *